US00PP28488P3

(12) United States Plant Patent
Hanes

(10) Patent No.: US PP28,488 P3
(45) Date of Patent: Oct. 3, 2017

(54) ***PELARGONIUM* PLANT NAMED 'PEQZ0011'**

(50) Latin Name: *Pelargonium interspecific*
Varietal Denomination: PEQZ0011

(71) Applicant: SYNGENTA PARTICIPATIONS AG, Basel (CH)

(72) Inventor: Mitchell E. Hanes, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/999,663

(22) Filed: Jun. 9, 2016

(65) Prior Publication Data

US 2016/0366802 P1 Dec. 15, 2016

(51) Int. Cl.
*A01H 5/02* (2006.01)

(52) U.S. Cl.
USPC ..... Plt./324

(58) Field of Classification Search
USPC ..... Plt./324
See application file for complete search history.

(56) References Cited

PUBLICATIONS

PLUTO Plant Variety Database Apr. 26, 2017.*

* cited by examiner

*Primary Examiner* — Annette Para
(74) *Attorney, Agent, or Firm* — Dale Skalla

(57) ABSTRACT

A new *Pelargonium* plant named 'PEQZ0011' particularly distinguished by the bright scarlet double petal inflorescences held above the medium-green foliage with a leaf zone that is very heat and drought tolerant with continuous color through the most extreme summer heat, on a well-branched plant habit.

1 Drawing Sheet

Latin name of the genus and species of the plant claimed: *Pelargonium interspecific.*

Varietal denomination: 'PEQZ0011'.

BACKGROUND OF THE NEW PLANT

The present invention comprises a new *Pelargonium*, botanically known as *Pelargonium interspecific*, and hereinafter referred to by the variety name 'PEQZ0011'.

'PEQZ0011' is a product of a planned breeding program. The new cultivar 'PEQZ0011' has intense scarlet double flower held above the green foliage on a well branched plant that is very heat and drought tolerant with continuous color.

'PEQZ0011' originates from a hybridization in a controlled breeding program made in August 2009, in a greenhouse in Gilroy, Calif. The female parent was an unpatented, proprietary plant of *P. interspecific* parentage, identified as '10707-1' with more open plant habit when compared to 'PEQZ0011'.

The male parent of 'PEQZ0011' was an unpatented, proprietary plant of *P. interspecific* parentage, identified as '10740-1' with bright scarlet colored florets and a more open plant habit when compared to 'PEQZ0011'. The resultant seed was sown in April 2010.

'PEQZ0011' was selected as one flowering plant within the progeny of the stated cross in July 2010 in a greenhouse in Gilroy, Calif.

The first act of asexual reproduction of 'PEQZ0011' was accomplished when vegetative cuttings were propagated from the initial selection in the September 2010 in a greenhouse in Gilroy, Calif.

BRIEF SUMMARY OF INVENTION

Horticultural examination of plants grown from cuttings of the plant initiated in Jun. 7, 2016 in Gilroy, Calif., and continuing thereafter, has demonstrated that the combination of characteristics as herein disclosed for 'PEQZ0011' are firmly fixed and are retained through successive generations of asexual reproduction.

'PEQZ0011' has not been observed under all possible environmental conditions. The phenotype may vary significantly with variations in environment such as temperature, light intensity, and day length.

A Plant Breeder's Right for this cultivar was applied for in the European Union on Jun. 10, 2015, No. 2015/1213. 'PEQZ0011' has not been made publicly available more than one year prior to the filing of this application.

The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

Figure 1:
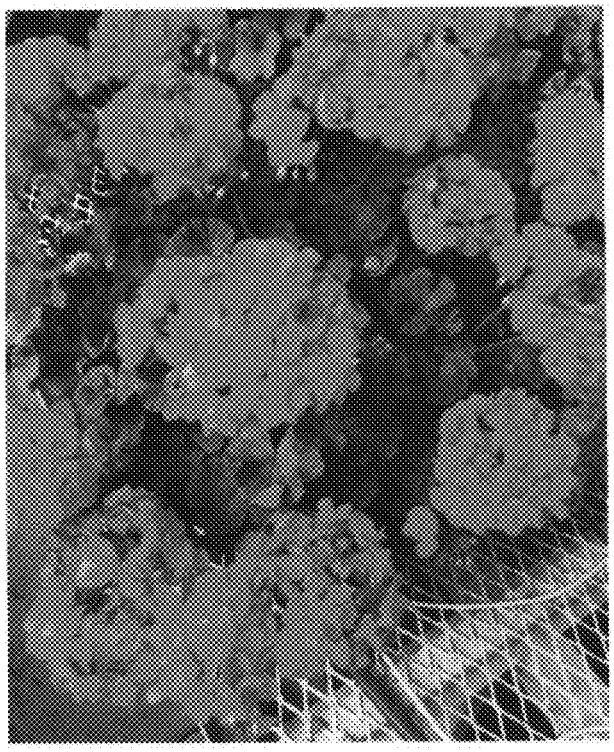
Figure 2:
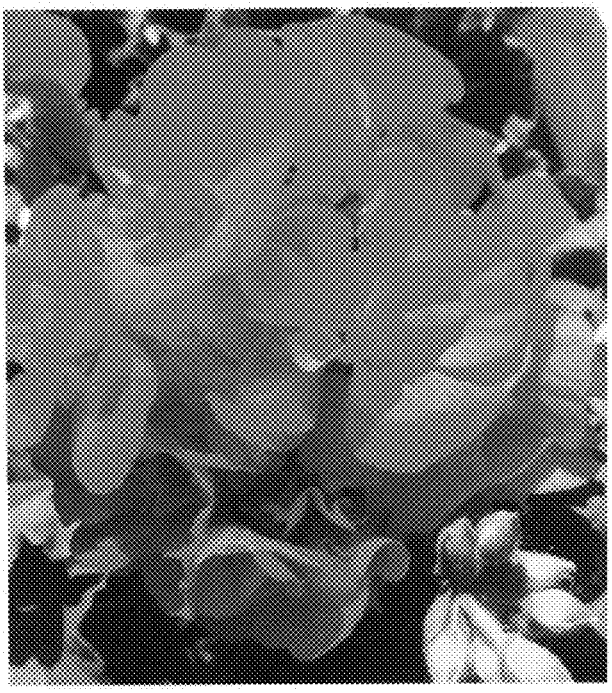

The accompanying photographic drawings show typical flower and foliage characteristics of 'PEQZ0011' with colors being as true as possible with an illustration of this type. The photographic drawings show in FIG. 1, 3 flowering plants of the new variety and in FIG. 2, a close-up of an inflorescence.

DETAILED BOTANICAL DESCRIPTION

The plant descriptions and measurements were taken in Gilroy, Calif. in Jun. 7, 2016 under natural light. These plants were approximately 7 weeks old and were grown in a 4 cell pack in a greenhouse trial.

Color references are made to The Royal Horticultural Society Colour Chart (R.H.S.) 2001.

Plant:

*Form, growth and habit.*—Upright, outwardly spreading and rounded growth habit, heat and drought tolerant with continuous color through the most extreme summer heat, edema tolerance, well-branched plant habit.

*Plant height.*—6 cm.

*Plant height (inflorescence included).*—13 cm.

*Plant width.*—12 cm.

Roots:

*Number of days to initiate roots.*—15-18 days at about 22 degrees C.

*Number of days to produce a rooted cutting.*—21-23 days at 22 degrees C.

*Type.*—Fine, fibrous, free branching.

*Color.*—RHS 156B.

Foliage:

*Immature leaf, color upper surface.*—Between RHS 137B and RHS 137C.

*Immature leaf, lower surface.*—RHS 138C.

*Mature leaf, color upper surface.*—RHS 137B.

*Mature leaf, color lower surface.*—RHS 137C.

*Length.*—4.5 cm.

*Width.*—6.2 cm.

*Shape.*—Reniform.

*Base shape.*—Reniform.

*Apex shape.*—Acute.

*Margin.*—Slightly dentate.

*Texture upper side.*—Hirsute.

*Texture lower side.*—Hirsute.

*Leaf zonation color.*—RHS N77A.

*Color of veins, upper surface.*—RHS 137B.

*Color of veins, lower surface.*—RHS 137C.

*Pattern of veining.*—Palmate.

*Petiole color.*—RHS 137D.

*Petiole length.*—4.1-6.0 cm.

*Diameter of petiole.*—0.3 cm.

*Texture.*—Pilose, hirsute, glandular hairs.

Stem:

*Quantity of branches.*—3.

*Color of stem.*—RHS 144B.

*Length of stem.*—2 cm.

*Diameter.*—0.7 cm.

*Length of internodes.*—0.5 cm.

*Texture.*—Sparsely hirsute, pilose, glandular hairs.

Peduncle:

*Color of peduncle.*—RHS 144A.

*Length of peduncle.*—9-10 cm.

*Peduncle diameter.*—0.2 cm.

*Texture.*—Hirsute, glandular hairs.

Pedicel:

*Color of pedicel.*—RHS 147C with reddish RHS 53A.

*Length of pedicel.*—2.3-3.2 cm.

*Diameter of pedicel.*—0.15 cm.

*Texture.*—Sparsely pilose, glandular hiars.

Bud (just before opening):

*Color.*—Between RHS 43A and RHS 44A.

*Length.*—1.5 cm.

*Width.*—0.7-0.8 cm.

*Shape.*—Elliptical.

Inflorescence:

*Type.*—Umbel; semi-spherical or nearly semi-spherical.

*Lastingness of individual flowers.*—7-9 days at 18° C. temperature.

*Number of inflorescences per plant.*—12, with 15 immature umbels in various stages.

*Fragrance.*—None.

*Umbel diameter.*—11 cm.

*Umbel depth.*—5.0 cm.

Corolla:

*Form.*—Double.

*Number of petals.*—9-11.

*Diameter of flower.*—About 5 cm.

*Depth of flower.*—1.5-2.0 cm.

*Color upper petals, upper surface.*—RHS 44A.

*Color upper petals, lower surface.*—RHS 44A.

*Length of upper petals.*—2.8 cm.

*Width of upper petals.*—2.3 cm.

*Color lower petals, upper surface.*—RHS 44A with brighter color.

*Color lower petals, lower surface.*—RHS 44B.

*Length of lower petals.*—2.2 cm.

*Width of lower petals.*—1.6 cm.

*Petal shape.*—Obovate to spathulate.

*Apex shape.*—Rounded.

*Margin.*—Entire.

*Base.*—Attenuate.

*Petal texture.*—Papillose on both surfaces.

Calyx:

*Number of sepals.*—5.

*Color of sepals.*—RHS 144A.

*Length of sepals.*—1.1 cm.

*Width of sepals.*—0.4 cm.

*Sepal shape.*—Lanceolate to linear.

*Apex shape.*—Acute.

*Margins.*—Mostly fused.

*Texture, upper surface.*—Glabrous.

*Lower surface.*—Glandular hairs, hirsute.

Reproductive organs:

Gynoecium:

*Pistil.*—1.

*Length.*—0.9 cm.

*Style color.*—RHS 53D.

*Style length.*—0.8 cm.

*Stigma color.*—RHS 44A.

*Ovary color.*—RHS 144B.

*Ovary length.*—0.5 cm.

*Ovary diameter.*—0.2 cm.

Androecium:

*Number of stamens.*—7-8.

*Color of filaments.*—RHS N155C.

*Length filaments.*—0.6 cm.

*Anther color.*—RHS 41C.

*Length of anthers.*—0.2 cm.

*Color of pollen.*—RHS 25B.

*Pollen amount.*—Normal.

*Fertility/seed set.*—Has not been determined to date.

*Disease/pest resistance.*—Has not been determined to date.

What is claimed is:

1. A new and distinct variety of *Pelargonium* plant named 'PEQZ0011' substantially as illustrated and described herein.

* * * * *